United States Patent
Maki, Jr.

[19]

[11] Patent Number: 5,874,676
[45] Date of Patent: Feb. 23, 1999

[54] METHOD AND APPARATUS FOR ACOUSTICALLY INVESTIGATING A CASING WITH A SWEPT FREQUENCY PULSE

[76] Inventor: Voldi E. Maki, Jr., 11904 Bell Ave., Austin, Tex. 78759-2415

[21] Appl. No.: 855,864

[22] Filed: May 12, 1997

[51] Int. Cl.6 ................................................ G01V 1/40
[52] U.S. Cl. .................... 73/579; 73/152.57; 73/152.58; 73/152.59; 367/35; 181/105; 702/6; 702/8
[58] Field of Search .......................... 73/152.57, 152.58, 73/152.59, 579; 367/35; 181/104, 105; 364/422; 702/9, 11, 6, 8

[56] References Cited

U.S. PATENT DOCUMENTS

| | | | |
|---|---|---|---|
| 2,484,623 | 10/1949 | Heising | 73/630 |
| 2,538,114 | 1/1951 | Mason | 73/630 |
| 3,914,987 | 10/1975 | Bickel et al. | 73/630 |
| 4,255,798 | 3/1981 | Havira | 367/35 |
| 4,382,290 | 5/1983 | Havira | 367/35 |
| 4,709,357 | 11/1987 | Maki, Jr. | 367/35 |
| 4,733,380 | 3/1988 | Havira | 367/35 |
| 4,916,648 | 4/1990 | Gard | 367/35 |
| 4,970,695 | 11/1990 | Huau | 367/13 |
| 5,146,432 | 9/1992 | Kimball | 367/13 |
| 5,491,668 | 2/1996 | Priest | 367/35 |
| 5,591,913 | 1/1997 | Tucker | 73/628 |

*Primary Examiner*—Hezron Williams
*Assistant Examiner*—Rose M. Miller
*Attorney, Agent, or Firm*—Baker & Botts, L.L.P.

[57] ABSTRACT

An apparatus and method for using swept frequency energy to inspect a casing or other body is disclosed. A transducer (75) transmits a swept frequency pulse at a casing and receives the reflection resulting from the pulse's impact against the casing. The reflected energy is translated to a reflection signal and analyzed by a signal processor having an envelope detector (240) which translates the reflection signal into an envelope signal. A microprocessor (260) located within the signal processor analyzes the envelope signal to compute data such as the thickness of the casing and the quality of the cement bond holding the casing.

20 Claims, 5 Drawing Sheets

METHOD AND APPARATUS FOR ACOUSTICALLY INVESTIGATING A CASING WITH A SWEPT FREQUENCY PULSE

TECHNICAL FIELD OF THE INVENTION

This invention relates in general to the field of acoustic well logging, and more particularly to a method and apparatus for measuring casing thickness and the quality of the cement bond holding the casing in place through the application of acoustic techniques.

BACKGROUND OF THE INVENTION

Petrochemicals are recovered from boreholes drilled into the earth. When first drilled, a new borehole, commonly referred to as an open hole, is tested for the presence of petrochemicals, including tests to determine producing zones within the borehole if petrochemicals are found. Such open-hole testing is accomplished with logging tools, called open-hole tools, such as an induction tool, a sonic tool, and a neutron tool. Open-hole tools are introduced into the borehole with an open-hole truck. Assuming producing zones are identified with the open-hole tools, the borehole is prepared for production by inserting a pipe, known as a casing, into the borehole, and then setting the casing by forcing cement into the annulus between the borehole and the casing. During production, petrochemicals are pumped through the casing and recovered at the surface.

Once the well begins producing petrochemicals, it is maintained and operated with production logging tools, using a case-hole truck. Production logging tools are much less expensive than open-hole tools, and much less complex. For instance, production logging tools operate using a mono-cable, typically less than a quarter of an inch in diameter, that interfaces with a case-hole truck. In contrast, open-hole tools require a multi-conductor cable, which is a cable approximately one-half of an inch in diameter, capable of transmitting much more data from the open-hole tools to the larger open-hole truck.

During production, the casing and the cement bond holding the casing in place act as a barrier to separate oil and gas producing zones from each other, and also from water bearing strata. If the cement and casing fail to provide this separation, fluids under pressure in one zone can migrate to another zone. This can present a serious difficulty in a producing well. For instance, migration of water into a producing zone can render the well unproductive. Accordingly, once a casing and cement are inserted into a borehole, the well operator generally checks the quality of the casing and cement bond before initiating production, and periodically thereafter.

A variety of acoustic techniques have been developed to test the casing and cement bond, as are disclosed in U.S. Pat. No. 4,709,357, issued to Maki, Jr., which is incorporated herein by reference. Generally, these techniques employ a short pulse of acoustic energy against the interior of the casing, the pulse having a frequency range selected to stimulate the radial casing thickness into resonance. The returns or reflections of the pulse are received and transmitted up hole for analysis to determine the thickness of the casing and the quality of the cement bond. However, these known acoustic techniques require considerable processing to calculate casing thickness and cement bond quality, and are thus slow and expensive to employ. For instance, U.S. Pat. No. 4,709,357 by Maki, Jr. discloses a filter designed to decrease the lengthy computation time associated with the integration techniques used in analyzing reflections of short duration pulses. Further, these known acoustic techniques generally need an open-hole truck, since many measured signal values must be sent to and analyzed by a processor located up-hole outside of the borehole. The analysis can include complex mathematical equations, which can use large amounts of processing capacity and take an extended period of time.

SUMMARY OF THE INVENTION

Therefore, a need has arisen for a casing inspection tool which can process acoustic information down hole, and send inspection results up hole through a simple mono-cable connection.

A further need exists for a casing inspection tool that rapidly inspects a casing through techniques that require relatively small amounts of processing capacity and time.

In accordance with the present invention, a casing inspection tool and method of inspecting a casing are provided that substantially eliminate or reduce disadvantages and problems associated with previously developed acoustic techniques for measuring a casing's thickness, and the quality of the cement bond holding the casing in place. A signal processor instructs an acoustic energy device to transmit swept-frequency acoustic energy against a casing and to retrieve reflection signals from the acoustic energy device. The signal processor analyzes the reflection signals to compute inspection data.

More specifically, the present invention provides a body for entering a casing, the body having an acoustic energy device, such as a transducer, that transmits swept frequency acoustic energy against the interior of a casing, receives reflected acoustic energy resulting from the reflection of the swept frequency acoustic energy against the casing, and translates the reflected acoustic energy into a reflection signal. A signal processor interfaced with the acoustic energy device retrieves and analyzes the reflection signal to compute casing inspection data from which the casing's thickness and the quality of the cement bond holding the casing in place can be computed. The signal processor can analyze the reflection signals to create an envelope signal having changes in amplitude, and can use the location and size of the changes in amplitude along the envelope signal to determine the thickness of the casing and quality of the cement bond to the casing. The thickness and quality inspection data can then be transmitted up-hole to the well operator.

The present invention provides several important technical advantages. The use of swept frequency acoustic energy permits calculation of thickness and cement bond quality inspection data with very little signal processing. The processing that is required can be accomplished through a simple program, such as analog circuits hardwired into the casing inspection tool or a short software program loaded on a memory chip in the casing inspection tool, thereby allowing casing inspection data to be calculated in the tool itself and then sent up hole through a simple connection such as a mono-cable. The necessary calculations to create casing inspection data from the reflection signal can be accomplished much quicker than the analysis techniques commonly employed by other acoustic inspection devices, thus allowing a quicker and more effective casing inspection.

Further, the simpler calculations to obtain inspection data using the swept frequency acoustic energy can be reached using less complicated and less expensive equipment, such as case-hole equipment, which generally has a greater degree of reliability than complicated, open-hole equipment otherwise used.

BRIEF DESCRIPTION OF THE DRAWINGS

A more complete understanding of the present invention and advantages thereof may be acquired by referring to the following description taken in conjunction with the accompanying drawings, in which like reference numbers indicate like features, and wherein.

DETAILED DESCRIPTION OF THE PREFERRED EMBODIMENT

Preferred embodiments of the present invention are illustrated in the figures, like numerals being used to refer to like and corresponding parts of the various drawings.

The present invention allows the inspection of a casing or other body having a resonant frequency by taking advantage of the changes in amplitude that occur in a reflection of a swept frequency pulse of energy off of the body or casing. A swept frequency pulse has a changing frequency over the duration of the pulse. For instance, in one embodiment, a transducer functions as an acoustic energy device that acts as an acoustic transmitter by translating electronic signals into corresponding acoustic energy and also acts as an acoustic receiver by translating received acoustic energy into electronic signals. A signal processor interfaced with the transducer receives the reflection signal created by the reflection of swept frequency acoustic energy off of the casing or body, and analyzes the reflection signal. By comparing the amplitude of the reflected signal against a predicted amplitude based upon the resonance for the material's thickness, the actual thickness of the material can be determined.

Figure 1:
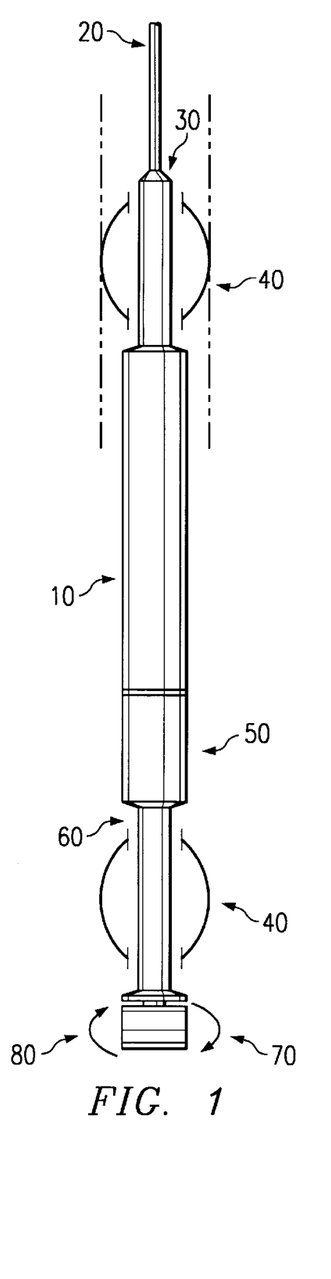
FIG. 1 is a side view of one embodiment of a casing inspection tool according to the present invention suspended from a cable.

Referring now to FIG. 1, a side view of one embodiment of the casing inspection tool is shown. A cylindrical body 10 is suspended from a cable 20 at a cable attachment point 30. The body 10 is adapted to fit into the casing to be inspected and, accordingly, has a diameter less than the diameter of the casing. The body 10 is adapted to contain a signal processor that directs the transmission of swept frequency energy and the reception and interpretation of reflection signals. A plurality of centralizers 40 maintain the position of the body 10 in the center of the casing. The cylindrical shape of the body 10 ensures that it will pass through the casing with the least amount of disturbance in or to the fluids present in the casing. However, other shapes and lengths of the body 10 can be adopted as necessary to accommodate the equipment interfaced with the body 10.

A motor 50 contained in the body 10 is coupled to a transducer housing 70 through a hollow shaft 60 extending from the bottom of the motor 50. The motor 50 receives electrical power through an interface with the body 10, thereby causing the transducer housing 70 to rotate around the vertical axis of the casing inspection tool, as depicted by arrow 80. In one embodiment, the motor 50 is a brushless direct current motor capable of rotating the transducer housing 70 at speeds of up to 800 revolutions per minute. The motor 50 includes a resolver to measure the location of the transducer housing 70 as it rotates and provide that location information through an electrical signal to the body 10. Other means of rotating the transducer housing 70, including other types of motors or rotating the body 10 as a whole, could also be used.

Transducer housing 70 holds a transducer 75 that is a wide band width design capable of producing a wide range of frequencies of acoustic energy at a generally constant amplitude. The transducer 75 produces acoustic energy responsive to electrical excitation voltage received through a wire passageway 78. Transducer 75 can also receive reflected acoustic energy and convert that energy into an electrical signal which can be transmitted to electronics in the body 10. Other means of producing acoustic energy and receiving acoustic reflections can be used.

Figure 2:
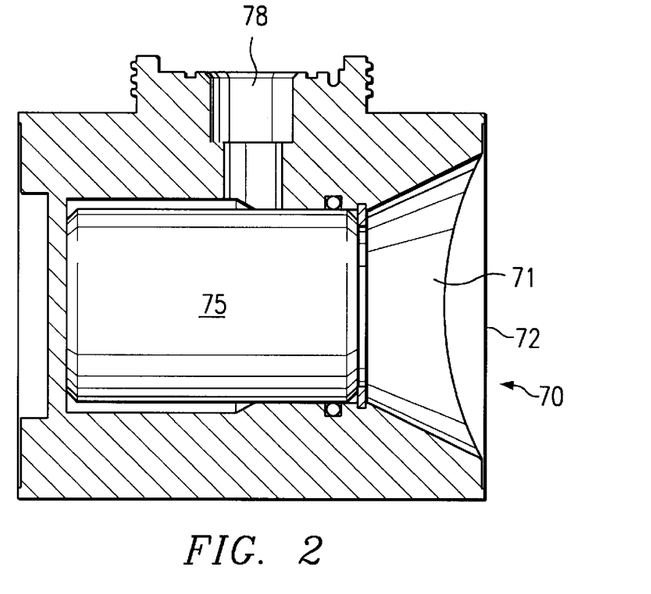
FIG. 2 is a cross sectional view of one embodiment of a body that holds a transducer.

Referring to FIG. 2, a cross sectional view of transducer housing 70 is shown. Transducer 75 emits acoustic energy through an opening 71 having a membrane 72 formed with a thin sheet of stainless steel covering the opening 71. Transducer 75 emits acoustic energy in segments approximately 10 degrees in width. The acoustic energy travels through borehole fluid in the opening 71 and then through the membrane 72 of thin stainless steel before passing through borehole fluid and into the casing to be inspected. The thin sheet of stainless steel acts as a membrane which reduces the turbulence that occurs when the transducer housing 70 is rotated in the borehole fluid. The membrane 72 may be designed to provide a calibration surface or be designed to appear transparent to acoustic energy.

Figure 3:
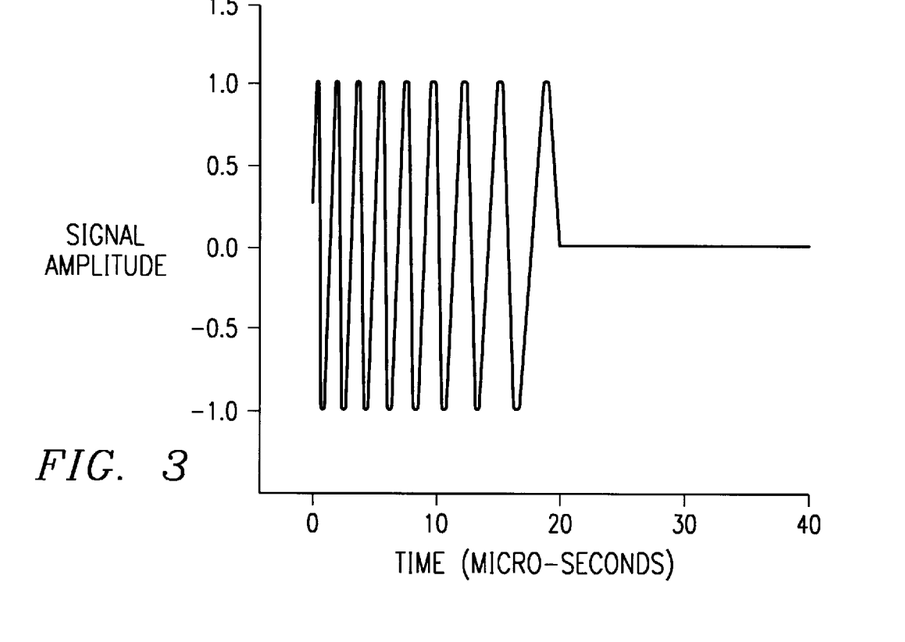
FIG. 3 depicts the amplitude and frequency of one possible swept frequency pulse source signal.

Referring now to FIG. 3, a time wave form of one type of acoustic energy that can be sent by transducer 75 is shown. The wave form lasts approximately 20 microseconds and initially has a high frequency which transitions to a low frequency over the duration of the wave form. The frequency range of the wave form is approximately 700 kilohertz at the initial high frequency and transitions down to a low final frequency of 200 kilohertz, and is designed to cover the resonant frequency of the casing being inspected when the casing resonates in the thickness mode as described herein. The wave form of FIG. 3 also has a generally constant amplitude through its duration. In summary, the wave form of FIG. 3 is a swept frequency pulse or chirp wave form which creates a chirp sound when transmitted from the transducer 75. However, other swept frequency wave forms can be used, including wave forms that transition from a low frequency to a high frequency or that have other transitions between varying frequencies.

Figure 4:
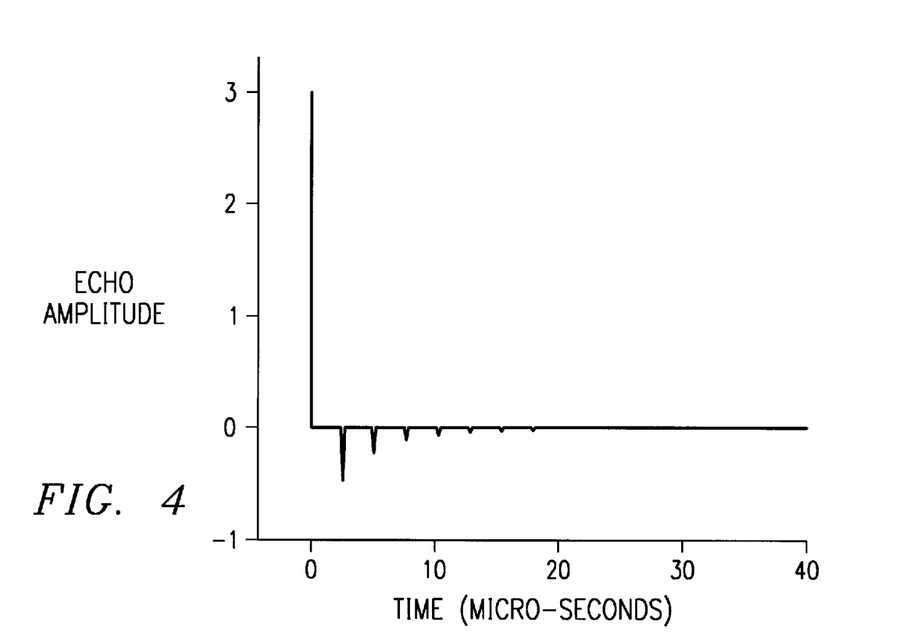
FIG. 4 depicts the echo structure of a 0.3-inch thick casing with a good quality cement bond.
Figure 4A:
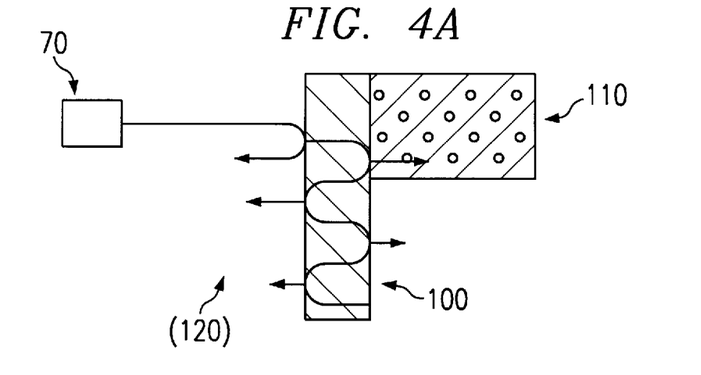
FIG. 4A depicts a casing that can produce the echo structure depicted in FIG. 4.

FIG. 4 shows the echo structure of a 0.3 inch thick casing set in good cement. FIG. 4A depicts acoustic energy transmitted from transducer 75 against casing 100 set in cement 110. The signal arriving at casing 100 is partially reflected and partially transmitted into casing 100. Thereafter, each time the reflected signal intersects an interface between two materials of differing acoustic impedances, the signal is partially reflected and partially transmitted. Essentially, the signal bounces back and forth in the steel of the casing, each time losing some of its energy alternately to the inside of the casing and to the outside of the casing. The rate at which the signal loses energy is related to the acoustic impedances of the casing, the borehole fluid 120 and the cement bond of the casing. A high quality cement bond has greater acoustic impedance than a low quality cement bond; thus, a high quality cement bond causes the signal to lose energy at a greater rate, known as a ring-down rate.

FIG. 4 depicts the mechanism of the reflections from within the casing, that would occur with a 0.3 inch thick casing set in good cement. In contrast, a casing having the same thickness set in poor cement would have a slower ring-down with each ring-down reflection having a greater amplitude than the reflections depicted in FIG. 4.

The frequency of the reflections, as opposed to the amplitude of the reflections, is related to the thickness of the casing rather than the quality of the cement bond. Thus, the ring-down signal received from a casing set in good cement will have the same ring-down frequency as a casing set in poor cement.

Figure 5:
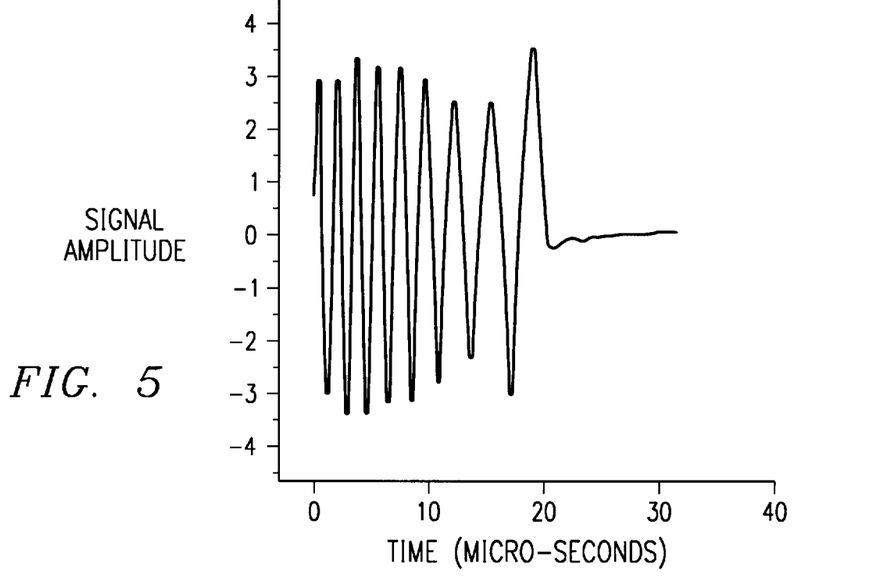
FIG. 5 depicts the swept frequency pulse of FIG. 3, convolved with the echo structure of FIG. 4.

FIG. 5 shows a reflection which could occur from the casing depicted in FIG. 4A being submitted to the pulse of FIG. 3. The amplitude of the reflected signal varies across its duration time and is related to the frequency of the swept frequency pulse and the resonant frequency of the casing. As the frequency of the swept frequency pulse depicted in FIG. 3 decreases over the duration of the pulse, it is equal to frequencies above and below the resonant frequency of the casing, causing the amplitude of the reflection to vary accordingly. Thus, the change in amplitude of the reflected signal over time is related to the thickness of the casing.

The reflection signal of FIG. 5 can also be predicted based upon the swept frequency pulse transmitted in FIG. 3 and the predicted echo structure of the casing depicted in FIG. 4. FIG. 5 results when the swept frequency pulse source signal is convolved with the echo structure. In the frequency domain, the two signals are convolved by taking the product of the spectra. In the time domain, the two signals are convolved by taking the sum of the products of the amplitudes of the source signal of FIG. 3 and the echo structure at each time domain sample point of each wave form, a signal processing technique that is well-known in the art.

Figure 6:
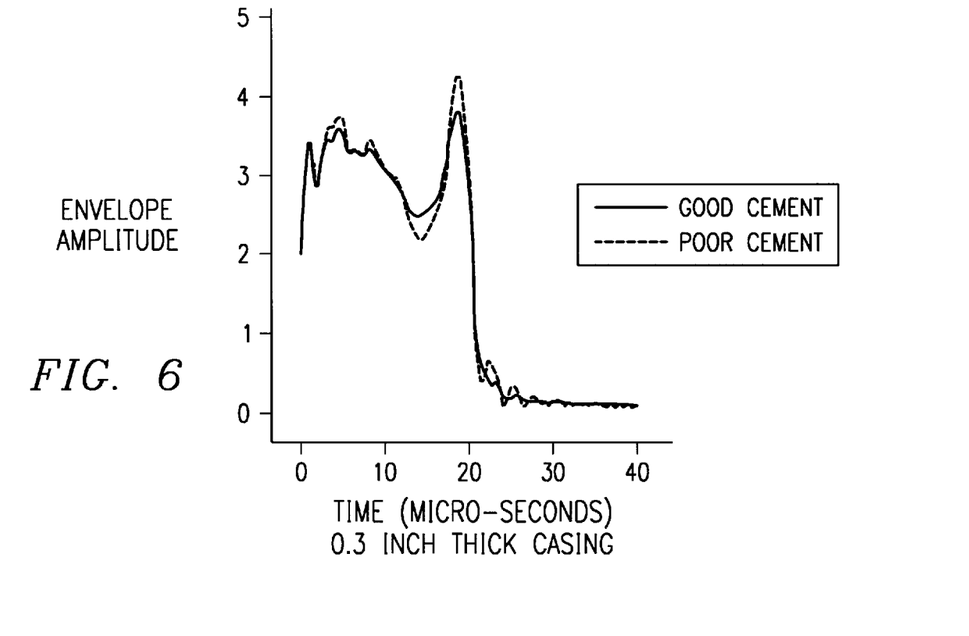
FIG. 6 depicts the envelope of the signal depicted in FIG. 5.

FIG. 6 shows the reflection signal envelope that results from the reflected signal shown in FIG. 5. The envelope is simply a trace of the amplitude of the reflected signal over the duration time. The basic structure of the envelope is a square pulse with a dip in amplitude which is related to the resonance of the casing. The magnitude of the dip in the envelope is related to the quality of the cement bond on the outside of the casing. A casing set in a poor bond has ring-down signal with a greater duration and, therefore, a greater amplitude across the duration of the signal than does a casing set in a good bond. This characteristic causes a greater dip in the amplitude of the reflection that occurs from a casing set in a poor bond when the casing is subjected to frequencies that approximate the resonant frequency of the casing than occurs in a casing set in good cement. The dash line of FIG. 6 illustrates the amplitude of the dip associated with a poor cement bond. In contrast, the solid line of FIG. 6 illustrates the dip in magnitude of the envelope which occurs when the casing is set in a good cement bond having a shorter ring-down period with a lower amplitude.

Figure 7:
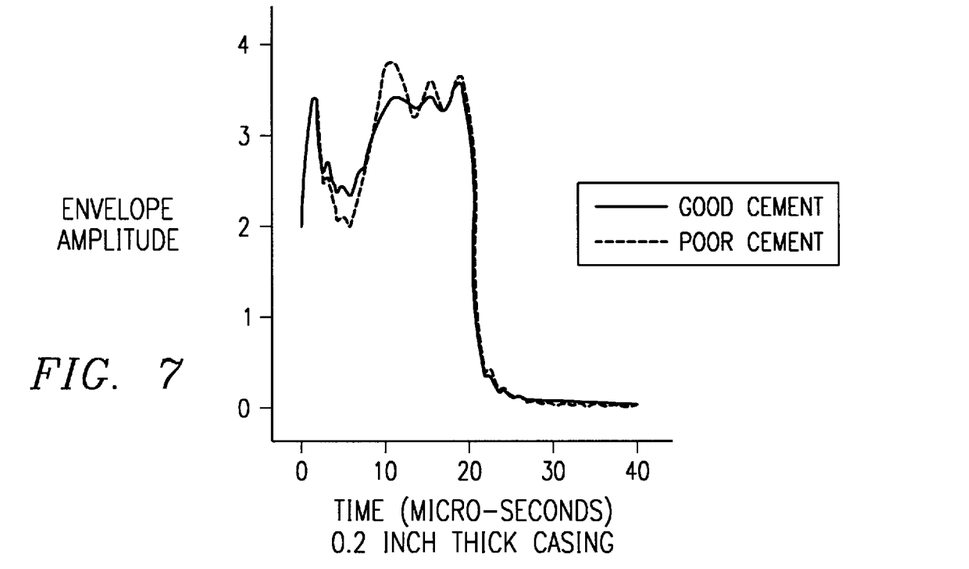
FIG. 7 depicts the envelope resulting from a 0.2-inch thick casing placed in cement.

Referring now to FIG. 7, the envelope of a reflected signal from a casing 0.2 inches thick set in good and poor cement is shown. The thinner casing of FIG. 6 has a dip in amplitude that occurs earlier in the duration of the reflected signal. Referring to FIG. 4A, the earlier dip occurs because the thinner casing has a higher reflection frequency and, thus, resonates at a higher frequency. Accordingly, the location of a dip in the amplitude of a reflected signal along its duration can be used to identify the thickness of the casing reflecting the signal. The solid and dotted lines indicate that the magnitude of the dip in amplitude still provides information regarding the cement bond quality in which the casing is set.

Figure 8:
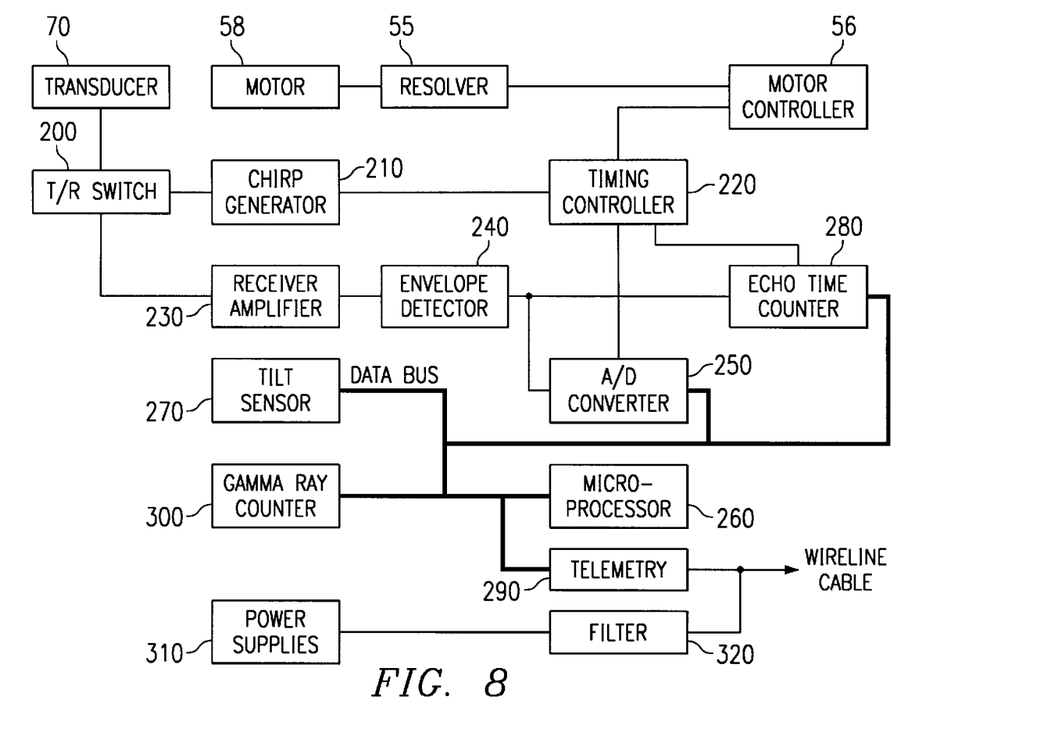
FIG. 8 presents a block diagram of the down-hole electronics.

Referring now to FIG. 8, a block diagram of one embodiment of the down-hole electronics is shown. The down-hole electronics of FIG. 8 act as the inspection tool's signal processor and can be stored in a cavity formed in the body (10) or in another convenient and protected location.

Transducer 75 is interfaced with a transmit/receive switch 200 which allows transducer 75 to operate alternatively in a transmit mode and a receive mode. Chirp generator 210 is interfaced with transmit/receive switch 200 and provides transmit/receive switch 200 with a high voltage electronic signal which the transducer 75 can use to produce the desired swept frequency pulse. Timing controller 220 sends a start pulse to the chirp generator 210 to send the swept frequency pulse through the transmit/receive switch 200 and to transducer 75. Resolver 55 sends a signal to a motor controller 56 which provides power to the motor and determines the position of the transducer housing 70 coupled to the motor 58 and provides this position data through an electronic signal sent to timing controller 220. In this way, timing controller 220 can ensure that acoustic energy is transmitted against the casing at predetermined points as the transducer 75 rotates in the casing. The rotation rate is also controlled by motor controller 56.

Transmit/receive switch 200 is also interfaced with receiver/amplifier 230. When chirp generator 210 is not providing a signal to transmit/receive switch 200, transmit/receive switch 200 instructs transducer 75 to receive reflection signals. The transducer 75 translates received reflection signals into electronic signals, and sends the reflection signals to receiver/amplifier 230, which amplifies the reflection signal and provides the amplified reflection signal to an envelope detector 240. The envelope detector 240 takes the reflection signal and full wave detects the amplitude of the signal to calculate an envelope signal. The envelope signal is converted to a digital signal through analog-to-digital converter 250 where it is then provided to microprocessor 260. Tilt sensor 270 detects the position of the casing inspection tool relative to vertical. Since even vertical wells are seldom vertical, at any given depth, one side of the well can be determined with a tiltmeter to be the "high side." By referencing all measurements to the "high side" of the well, any work done later can be located circumferentially using this same technique.

Timing controller 220 is also interfaced with echo time counter 280. When timing controller 220 instructs chirp generator 210 to transmit a signal to transducer 75, echo time counter 280 also receives this instruction and initiates a clock. When envelope detector 240 receives the reflected signal from transducer 75, it provides the reflected signal to echo time counter 280, allowing echo time counter 280 to measure the time of flight of the pulse, meaning the time between the transmission of the chirp pulse and the reception of the reflected signal. This pulse time of flight measurement is provided to the microprocessor 260 and can be used to detect the diameter of the casing.

Microprocessor 260 analyzes the digitized envelope signal to compute the casing thickness and the condition of the cement bond on the outside of the casing. These two casing inspection data points and the digitized pulse time of flight are provided to a telemetry unit for transmission up hole through the cable 20, along with tilt sensor data generated by tilt sensor 270, and gamma ray data generated by gamma ray counter 300. The gamma ray data is used for reference to previous logs.

The down-hole electronics are each provided with appropriate power voltages through power supply 310. Filter 320 isolates the direct current power provided by power supply 310 from the high frequency signal which transmits the telemetry data. The cable 20 can be a mono-cable which provides power to power supply 310 and which provides a conduit for telemetry data transmitted from telemetry unit 290. Cable 20 also provides a conduit for commands from up hole to be transmitted down hole to microprocessor 260.

Figure 9:
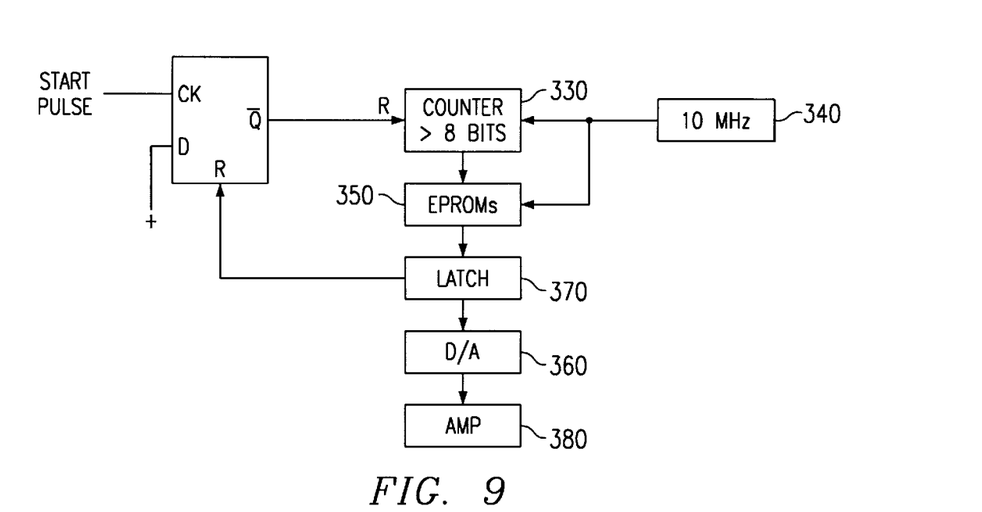
FIG. 9 depicts one embodiment of a circuit for creating a chirp wave form.

One embodiment of a circuit that will generate and transmit the desired chirp wave form is depicted in FIG. 9. This circuit consists of a Dual Port Random Access Memory or EPROM which interfaces with a digital to analog converter. The microprocessor 260 either creates or selects a chirp wave form. Timing controller 220 provides a short start pulse to initiate a chirp wave form. Referring to FIG. 9, a counter 330 is interfaced with an oscillator 340 and a flip flop and an EPROM 350 which has the desired sine wave stored in memory. Upon initiation by timing controller 220, the counter puts addresses into EPROM 350, which clocks out the chirp wave form to digital to analog converter 360. The latch 370 buffers the EPROM signal to remove transitions caused by differing delays in individual bits from the EPROM. When the end of a waveform occurs, an extra bit from the EPROM resets the flip flop and the counter. The signal at the output of the digital to analog converter 360 has the correct shape but is not large enough in amplitude. An amplifier 380 increases the amplitude of the signal from about 1 vpp to over 300 vpp.

In operation, the casing inspection tool is suspended down the vertical axis of the casing by cable 20 and centered in the casing by centralizer 40 thereby aiming the transmitter/receiver of transducer 75 at the casing on an axis generally perpendicular to the vertical axis of the casing inspection tool. Motor 50 in body 10 rotates transducer housing 70 around the vertical axis of the casing inspection tool. Resolver 55 provides the rotational position of motor 50 to motor controller 56 which provides timing pulses to timer controller 220. At a predetermined position, timer controller 220 directs chirp generator 210 to send a high voltage swept frequency pulse to transmit/receive switch 200, which in turn directs transducer 75 to enter a transmit mode and transmit a swept frequency pulse of acoustic energy corresponding to the chirp signal towards the casing. Timing controller 220 passes the transmission signal to echo time counter 280, which begins its travel time count. Upon completion of the transmission, transmit/receive switch 200 directs transducer 75 to resume a receive mode.

The swept frequency pulse of acoustic energy travels through the bore hole fluid held within the casing and impacts the membrane of the thin sheet of stainless steel 72. The thin sheet of stainless steel acts as a calibration membrane which allows the majority of the acoustic energy to pass through it and reflects a small amount of the acoustic energy back towards transducer 75. Transducer 75 receives this membrane reflection and passes a corresponding electronic signal through receiver/amplifier 230 and envelope detector 240 into echo time counter 280. Echo time counter 280 detects the arrival of the membrane reflection and calculates the sound velocity in the fluid by comparing the membrane arrival time against the known distance between the transducer and the membrane 72. Thin stainless steel membrane 72 can be made of other materials having similar reflection characteristics.

The remainder of the swept frequency pulse of acoustic energy passes through the bore hole fluid and impacts the casing, creating a reflection signal that travels back through the bore hole fluid to transducer 75 which provides the reflection signal to receiver/amplifier 230 for amplification. Receiver/amplifier 230 then provides the amplified reflection signal to envelope detector 240 which calculates the envelope signal and sends the envelope signal to echo time counter 280 and analog digital converter 250. Echo time counter 280 calculates the time between the transmission of the swept frequency pulse and the reception of the reflection signal and, using the calibration data derived from the membrane signal, calculates the time of flight of the swept frequency pulse corrected for the sound velocity of the fluid, and passes the time of flight to the microprocessor 260. Upon receiving this data, analog-to-digital converter 280 initiates the digitizing of the signal envelope and provides the signal envelope to microprocessor 260. Microprocessor 260 uses the signal envelope to determine the casing thickness and quality of the cement bond and then sends this data and the time of flight data up hole through telemetry unit 290. In alternative embodiments, the reflection signal can be sent up hole and processed at various points in the signal process logic. However, the amount of data which is required to be transmitted up hole forces the use of multi-conductor open hole cable. In another alternative embodiment, the microprocessor itself my take the travel time of the calibration and the travel time of the casing arrival and calculate a correct casing distance.

Motor controller 56 directs motor 50 to rotate transducer housing 70. When timer controller 220 determines that the position of transducer 75 has reached the next investigation point, based upon data provided from resolver 55, timing controller 220 directs chirp generator 210 to again send out a swept frequency pulse of energy. In this way, transducer 75 provides a swept frequency pulse every 10 degrees of rotation, allowing a thorough investigation of the casing at the level in the borehole where the transducer is being rotated. Once a complete rotation has occurred, the casing inspection tool can be altered to a higher or lower level in the casing by raising or lowering the cable as appropriate. In alternative embodiments, the casing can be inspected in larger or smaller increments as necessary.

The relatively simple calculations required to calculate the casing thickness and cement bond quality from reflections of a swept frequency pulse allow a more thorough inspection of a casing in less time with less expensive and less complicated equipment. For instance, the processing of the reflection data can be accomplished down hole, reducing the need to have high data rate conduits between the surface of the well and the inspection tool. The simple calculations allow more inspection points, so that corrosion in the casing can be analyzed in greater detail. The reduced time and expense associated with the present invention allows more frequent inspections, thus helping wells to run more efficiently with a reduced likelihood of costly failures.

Although the present invention has been described in detail, it should be understood that various changes, substitutions and alterations can be made hereto without departing from the spirit and scope of the invention as defined by the appended claims.

What is claimed is:

1. A casing inspection tool for inspecting a casing with acoustic energy, the tool comprising:
   a body adapted to enter a casing;
   an acoustic energy device coupled to said body, said acoustic energy device having an acoustic transmitter for transmitting acoustic energy and an acoustic receiver for receiving reflected acoustic energy and translating the reflected acoustic energy into a reflection signal; and
   a signal processor interfaced with said acoustic energy device, said signal processor providing instructions that:
      direct said acoustic energy device to transmit a swept frequency acoustic energy pulse at the casing;
      retrieve reflection signals from said acoustic energy device to said signal processor; and
      convolve the swept frequency pulse and the reflection signals to compute casing inspection data.

2. The tool according to claim 1 wherein the casing has a resonant frequency and wherein the swept frequency acoustic energy pulse transmitted by said acoustic energy device comprises a swept frequency pulse having a duration time and having an initial frequency greater than the resonant frequency of the casing, the initial frequency transitioning over the duration time to a final frequency less than the resonant frequency of the casing.

3. The tool according to claim 2 wherein said acoustic energy device comprises a transducer having a transmit mode and a receive mode, and wherein said signal processor comprises a transmit receive switch interfaced with said transducer to switch said transducer between the transmit mode and the receive mode.

4. The tool according to claim 3 wherein the casing inspection data comprises an envelope signal having a square pulse and a dip located along the square pulse, the dip having a magnitude.

5. The tool according to claim 4 wherein said signal processor analyzes the envelope signal to calculate a casing thickness related to the position of dip in the square pulse.

6. The tool according to claim 5 wherein the casing is set in cement and said signal processor analyzes the envelope signal to calculate a cement bond quality related to the magnitude of the dip.

7. An apparatus according to claim 6 further comprising an echo time counter interfaced with said signal processor, said echo time counter computing a pulse time of flight.

8. The apparatus according to claim 3 wherein the casing is set with cement in a borehole along a vertical axis, the apparatus further comprising a motor coupled to said transducer, said motor operationally rotating said transducer in a plane generally perpendicular to the vertical axis of the casing.

9. The apparatus according to claim 8 further comprising a calibration membrane located between said transducer and the casing, said transducer receiving a membrane reflection from said membrane and translating the membrane reflections to a calibration signal, said signal processor retrieving the calibration signal to calculate a fluid sound velocity.

10. The apparatus according to claim 8 wherein the signal processor is incorporated within the body.

11. An apparatus for inspecting a casing, the apparatus comprising:
    a transducer;
    a signal processor interfaced with the transducer, the signal processor having a program, the program instructing the signal processor to:
       direct the transducer to transmit swept frequency energy pulse;
       direct the transducer to receive reflection energy; and
       compare the swept frequency pulse and the reflection energy to calculate inspection data.

12. The apparatus according to claim 11 wherein the inspection data comprises the thickness of the casing.

13. The apparatus according to claim 11 further comprising a motor coupled to the transducer in order to rotate the transducer.

14. The apparatus according to claim 11 further comprising a membrane coupled to the transducer so that the transducer transmits the swept frequency energy through the membrane; and
    wherein the program of said signal processor directs the signal processor to analyze the reflection of the swept frequency energy from the membrane to calculate the velocity of the swept frequency energy.

15. A method for inspecting a body having a resonant frequency with swept frequency energy, the method comprising the steps of:
    directing swept frequency energy signal against the body;
    receiving reflections from the impact of the swept frequency energy against the body; and
    calculating inspection data by convolving the swept frequency energy signal and the reflections.

16. The method according to claim 15 wherein the swept frequency energy comprises acoustic energy having an initial frequency above the resonant frequency of the body, the initial frequency transitioning to a final frequency below the resonant frequency of the body.

17. The method according to claim 16 wherein the inspection data comprises the thickness of the body.

18. The method according to claim 16 wherein the body is set in cement, and the inspection data comprises the quality of the cement proximate to the body.

19. The method according to claim 16 wherein the acoustic energy is produced by a transducer.

20. The method according to claim 19 wherein the body subject to inspection is a casing set in a borehole with cement.

* * * * *